(12) United States Patent
Yamatani

(10) Patent No.: US 8,764,630 B2
(45) Date of Patent: Jul. 1, 2014

(54) ENDOSCOPIC SURGICAL PROCEDURE AND SURGICAL APPARATUS

(75) Inventor: Ken Yamatani, Tokyo (JP)

(73) Assignee: Olympus Medical Systems Corp. (JP)

( * ) Notice: Subject to any disclaimer, the term of this patent is extended or adjusted under 35 U.S.C. 154(b) by 1149 days.

(21) Appl. No.: 12/122,802

(22) Filed: May 19, 2008

(65) Prior Publication Data
US 2009/0287046 A1 Nov. 19, 2009

(51) Int. Cl.
*A61B 1/00* (2006.01)

(52) U.S. Cl.
USPC ........... 600/104; 600/103; 600/106; 600/107; 600/114; 604/104

(58) Field of Classification Search
USPC ........... 600/104, 201, 103, 106, 107, 114, 600/206–210; 604/104, 908; 606/191, 198, 606/192
See application file for complete search history.

(56) References Cited

U.S. PATENT DOCUMENTS

| | | | |
|---|---|---|---|
| 5,242,456 A | | 9/1993 | Nash et al. |
| 5,275,610 A | * | 1/1994 | Eberbach ............ 606/198 |
| 5,501,653 A | * | 3/1996 | Chin ............... 600/204 |
| 5,662,676 A | * | 9/1997 | Koninckx ............ 606/198 |
| 5,681,349 A | * | 10/1997 | Sugarbaker ............ 606/207 |
| 5,743,851 A | | 4/1998 | Moll et al. |
| 5,865,802 A | * | 2/1999 | Yoon et al. ............ 600/114 |
| 2001/0049492 A1 | * | 12/2001 | Frazier et al. ............ 604/104 |
| 2003/0225432 A1 | | 12/2003 | Baptiste et al. |
| 2004/0097792 A1 | * | 5/2004 | Moll et al. ............ 600/201 |
| 2004/0152977 A1 | * | 8/2004 | Duchon et al. ............ 600/431 |
| 2006/0069408 A1 | | 3/2006 | Kato |
| 2006/0184048 A1 | * | 8/2006 | Saadat ............ 600/478 |
| 2007/0060939 A1 | * | 3/2007 | Lancial et al. ............ 606/191 |
| 2007/0213584 A1 | | 9/2007 | Kim et al. |
| 2008/0249534 A1 | * | 10/2008 | Gruber et al. ............ 606/119 |

FOREIGN PATENT DOCUMENTS

| | | |
|---|---|---|
| FR | 2 726 993 | 5/1996 |
| JP | S60-168801 | 11/1985 |
| JP | 6-031705 | 4/1994 |
| JP | 6-507810 | 9/1994 |
| JP | 07-116262 | 5/1995 |

(Continued)

OTHER PUBLICATIONS

European Office Action dated Jul. 20, 2011 in corresponding European Patent Application No. EP 09 00 6724 (English language).
Extended European Search Report dated Jul. 21, 2009 in corresponding European Patent Application No. EP 09 00 6724 (English language).

(Continued)

*Primary Examiner* — Matthew J Kasztejna
*Assistant Examiner* — Kevin G Barry, III
(74) *Attorney, Agent, or Firm* — Ostrolenk Faber LLP

(57) ABSTRACT

A minimally invasive endoscopic surgical procedure or an endoscopic surgical procedure through natural orifices which includes: introducing a spacial structure in a shrunken state into a body cavity by a spacial structure introduction portion; enlarging the spacial structure in the body cavity; setting the enlarged spacial structure in a predetermined position in the body cavity and supporting the tissues inside of the body cavity with the set spacial structure; inserting a distal end of at least an endoscope or a treatment instrument from at least a part of an opening portion of the spacial structure, and orienting the distal end to a pathological lesion located on the inner side of the tissues inside of the body cavity which is supported by the spacial structure.

4 Claims, 11 Drawing Sheets

(56) References Cited

FOREIGN PATENT DOCUMENTS

| | | |
|---|---|---|
| JP | 08-336538 | 12/1996 |
| JP | 11-076246 | 3/1999 |
| JP | 2000-037388 | 2/2000 |
| WO | WO 92/21293 | 10/1992 |
| WO | WO 2005/104959 | 11/2005 |
| WO | WO 2007/083305 | 7/2007 |

OTHER PUBLICATIONS

Office Action issued by the Japanese Patent Office on May 22, 2012 in connection with corresponding Japanese Patent Application No. 2009-118920.

Translation of Office Action issued by the Japanese Patent Office on May 22, 2012 in connection with corresponding Japanese Patent Application No. 2009-118920.

* cited by examiner

ENDOSCOPIC SURGICAL PROCEDURE AND SURGICAL APPARATUS

BACKGROUND OF THE INVENTION

1. Field of the Invention

The present invention relates to an endoscopic surgical procedure and surgical apparatus.

2. Description of the Related Art

In recent years, endoscopic surgeries, such as cholecystectomy have been used, in which the inside of a body cavity is observed by an endoscope, internal organs are operated by treatment instruments or the like, and operations are performed. In such endoscopic surgeries, it is important to displace internal organs which are not related to the observation or the operation and assure a field of view and operative field by enlarging a narrow cavity. However, these are not big issues in general abdominal operations.

Specifically, the operations performed are namely; moving a body tissue or an internal organ located above observation or operation target with grasping forceps; slightly moving the internal organ or the like, which is not under observation or the operation target, during operations, with grasping forceps or the like; moving the internal organ or the like, which is not under observation or the operation target, with another grasping forceps or the like.

On these occasions, there are issues that the body tissue or the internal organ, which are not target of a treatment or the like, might be damaged. Also, a plurality of grasping forceps or the like is necessary for moving the body tissue or the internal organ, which is not target of a treatment or the like. Accordingly, other holes are necessary for inserting the grasping forceps or the like into the body, whereby there are issues of increasing the invasiveness of a patient.

As an apparatus for handling these issues, an instrument having an axis body, a hollow tube provided in a revolvable manner around the axis body, and a plurality of elastic striatums, one end of which being fixed to the axis body and the other end of which being fixed to the hollow tube, is proposed in Japanese Unexamined Patent Application, First Publication No. H08-336538. The apparatus proposed in the publication is able to select from a stored state in which the elastic striatum is constricted and an operation state in which the elastic striatum is enlarged by allowing the axis body and the hollow tube to rotate relatively. By selecting the operation state in which the elastic striatum is enlarged, it is possible to support the body tissue or the internal organ.

SUMMARY OF THE INVENTION

A first aspect of the present invention is an endoscopic surgical procedure in a minimally invasive endoscopic surgical procedure or an endoscopic surgical procedure through natural orifices which includes: introducing a spacial structure in a shrunken state into a body cavity by a spacial structure introduction portion; enlarging the spacial structure in the body cavity; setting the enlarged spacial structure in a predetermined position in the body cavity and supporting tissues inside of the body cavity with the set spacial structure; inserting a distal end of at least an endoscope or a treatment instrument from at least a part of an opening portion of the spacial structure and orienting the distal end to a pathological lesion located on the inner side of the tissues inside of the body cavity which is supported by the spacial structure.

A second aspect of the present invention is a surgical apparatus which includes: a spacial structure which is deformable to be shrunken or enlarged, when it is disposed in a body cavity in an enlarged state, it is possible to support tissues inside of the body cavity and to be temporarily placed in a body; a spacial structure introduction mechanism which is able to insert the spacial structure in a shrunken state into the body cavity; an endoscope or a treatment instrument, a distal end of which is inserted from an opening provided in the spacial structure disposed in the body cavity, the distal end is oriented to the pathological lesion located on the inner side of the tissues inside of the body cavity which is supported by the spacial structure.

DETAILED DESCRIPTION OF THE INVENTION

Each embodiment of the present invention shall be described below.

[First Embodiment]

Figure 1:
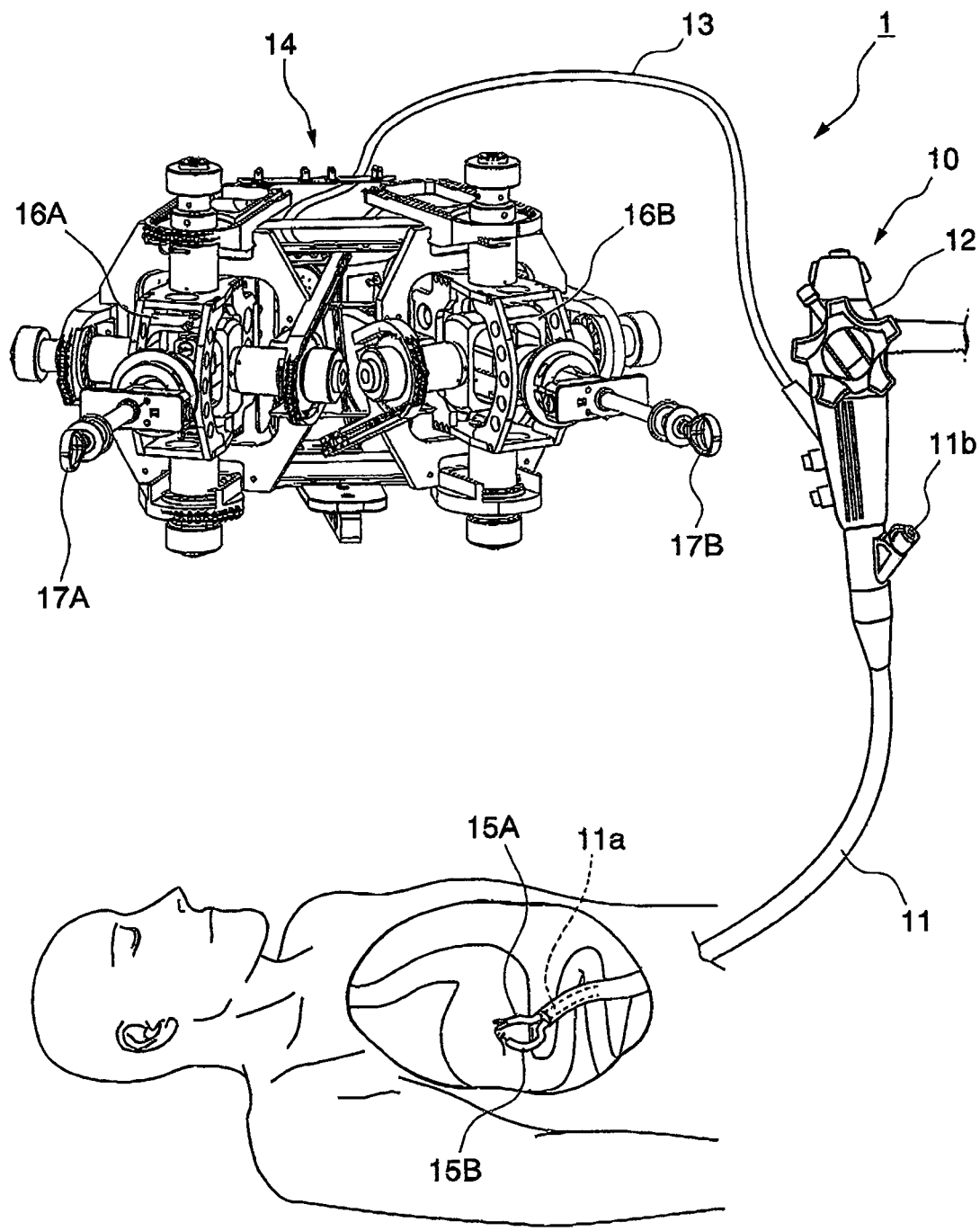
FIG. 1 shows an overview of a surgical apparatus in accordance with a first embodiment.

A first embodiment of the present invention shall be explained with reference to FIGS. 1 to 6. FIG. 1 is a perspective view showing the overall picture of a surgical apparatus in accordance with the first embodiment of the present invention. As shown in the figure, a surgical apparatus 1 includes: a treatment endoscope 10; a spacial structure 20 capable of supporting tissues inside of a body cavity when disposed in an arbitral position inside of the body cavity; a spacial structure introduction mechanism for inserting the spacial structure 20 in a shrunken state into the body cavity (refer FIG. 2).

Here, the spacial structure 20 is inserted into the body cavity by using a channel 11a of an insertion portion 11 of the treatment endoscope 10. That is, the treatment endoscope 10 has a function as the spacial structure introduction mechanism for inserting the spacial structure 20 into the body cavity.

The treatment endoscope 10 includes: the channel 11a; the insertion portion 11 which is inserted into the body cavity from a distal end thereof; an operation portion 12 for curving a distal end of the insertion portion 11; and a treatment instrument guide 14 for guiding right and left treatment instruments 17A and 17B into the insertion portion 11, via a pipe 13 and the operation portion 12, toward a front side of the distal end of the insertion portion 11. The treatment instrument guide 14 has right and left arms 15A and 15B which protrudes from the distal end of the insertion portion 11. The right and left arms 15A and 15B are independently curved right, left, up, and down by operating the first operation portions 16A and 16B on the proximal side of the treatment instrument guide 14. Also, by operating a second operation portion (not shown), the right and left arms 15A and 15B are selected from a straight state suitable for insertion into the body cavity or a curved state suitable for the treatment. Here, FIG. 1 shows each of the right and left arms 15A and 15B in the curved state. When the treatment instruments 17A and 17B are respectively inserted from the first operation portions 16A and 16B of the treatment instrument guide 14, the treatment instruments 17A and 17B pass the pipe 13, the operation portion 12, and the insertion portion 11 and distal ends thereof protrude forward from distal ends of the arms 15A and 15B.

Figure 3:
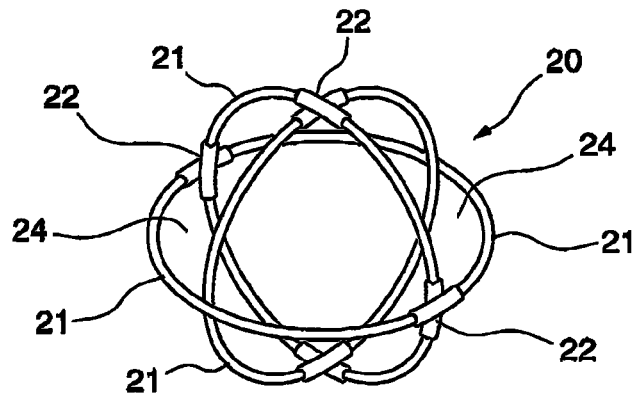
FIG. 3 is a perspective view showing an example of a spacial structure.
Figure 4:
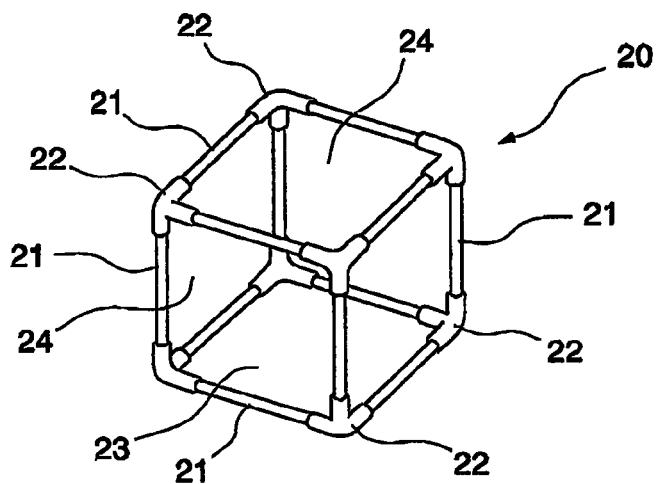
FIG. 4 is a perspective view showing another example of a spacial structure.
Figure 5:
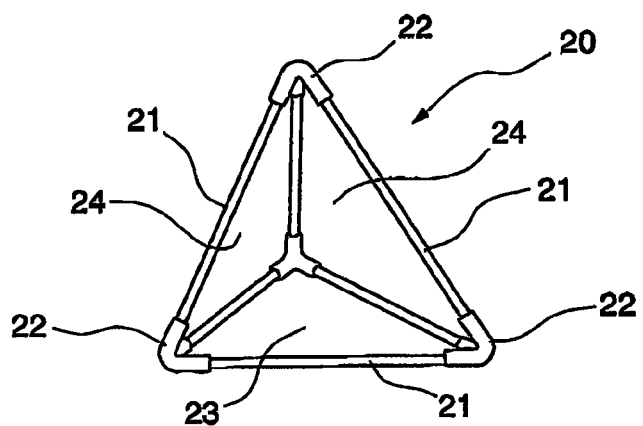
FIG. 5 is a perspective view showing another example of a spacial structure.

FIGS. 3 to 5 show specific structural examples of the spacial structure 20. The spacial structure 20 assures adequate space in the body cavity during procedures. For example, in the case of extracting the cholecyst, the spacial structure 20 supports the liver R located above the cholecyst, exposes the cholecyst inside of the body cavity, and assures space necessary for the treatment around the cholecyst. Specific structures for the spacial structure 20 includes, as shown in FIGS. 3 to 5, a plurality of rod members 21 made of elastic material, and connection portions 22 for connecting end portions of the rod members 21, for example. The rod members 21 and the connection portions 22 are flexible so that, when the entire spacial structure 20 is folded, the diameter of the spacial structure 20 is able to be inserted into the channel 11a of the insertion portion 11. Preferable materials for the rod members 21 and the connection portion 22 include shape-memory metal, a soft plastic material which is harmless to the human body, or the like. The entire shape of the spacial structure 20 includes a spherical shape as shown in FIG. 3, a rectangular hexahedron or a rectangular parallelepipe as shown in FIG. 4, or a three-sided pyramid as shown in FIG. 5. When the spacial structure 20 is the rectangular parallelepipe or the three-sided pyramid, since at least a flat portion 23 is formed on the outer surface thereof, it is advantageous in that it can be stably placed on a flat place in the body cavity.

Since these spacial structures 20 are formed by connecting the end portions of the rod members 21, which are assembled so as to interpose spaces therebetween, opening portions 24 are formed between the rod members 21. Also, when the spacial structure 20 is placed in the body cavity in the enlarged state so as to support the tissues inside of the body cavity such as internal organs in the body cavity, by using the opening portions 24, it is possible to orient the distal end of the endoscope or the treatment instrument to pathological lesion such as cholecyst A located on the inner side of the tissues inside of the body cavity supported by the spacial structure 20. (refer FIG. 2)

Here, although the above-described spacial structure 20 connects end portions of the rod members 21 by the connection portions 22, the structure of the spacial structure 20 is not limited to this, but the end portions of the rod members 21 can be directly glued with adhesives or brazing alloys.

Figure 6:
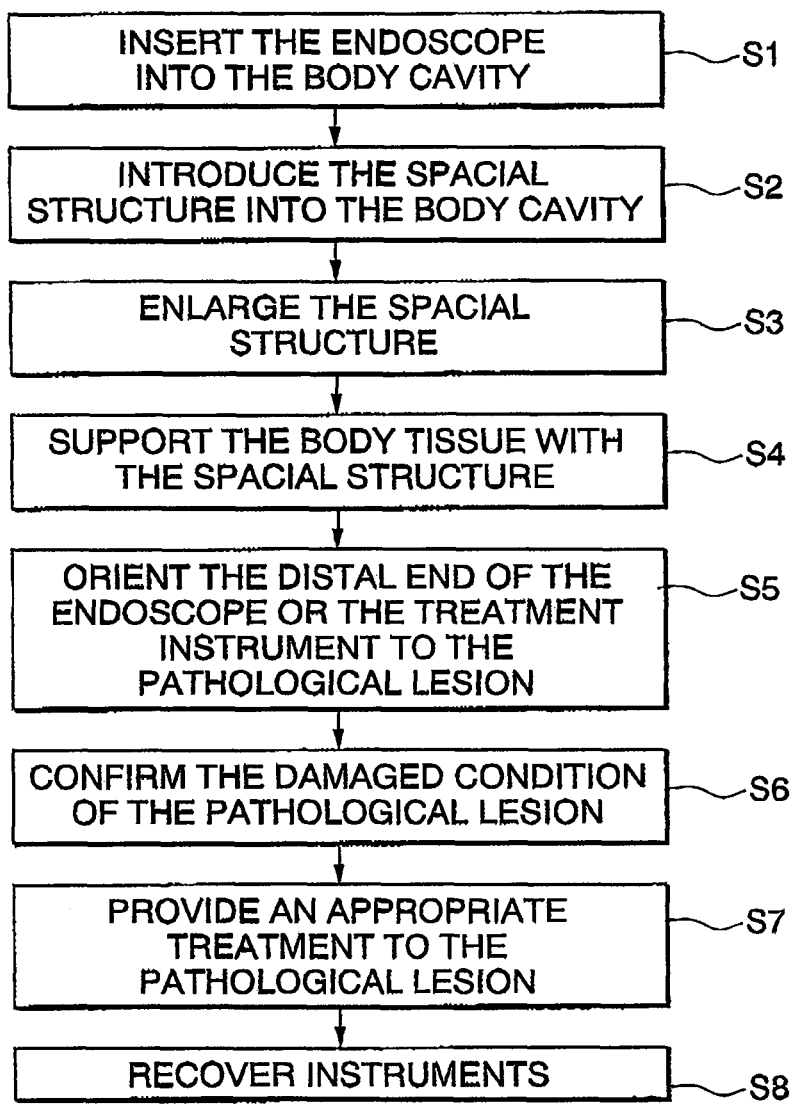
FIG. 6 is a flowchart showing a procedure of the endoscopic surgical procedure using the surgical apparatus.

Next, a procedure for treating the cholecyst A which is the pathological lesion by using the above surgical apparatus 1 shall be described with reference to FIG. 6.

First, the insertion portion 11 of the treatment endoscope 10 is inserted into a abdominal cavity by penetrating, for example, the umbilicus of the patient (step S1). At this moment, necessary treatment instruments such as grasping forceps may be provided to the treatment instrument 10 in advance, or the treatment instruments 17A and 17B may be set to the treatment endoscope 10 when the distal end of the insertion portion 10 is inserted to a required position in the body cavity.

Next, the abdominal portion of the patient is made to swell by sending air into the abdominal cavity. In this situation, the spacial structure 20 folded in advance is inserted from a forceps plug 11b of the insertion portion 11. Next, a pushing instrument such as a wire is inserted into the forceps plug 11b, and the spacial structure 20 is sent into the abdominal cavity by pushing the spacial structure 20 through the channel 11a (step S2). The spacial structure 20 sent into the abdominal cavity from the channel 11a enlarges by its own elasticity (step S3).

Figure 2:
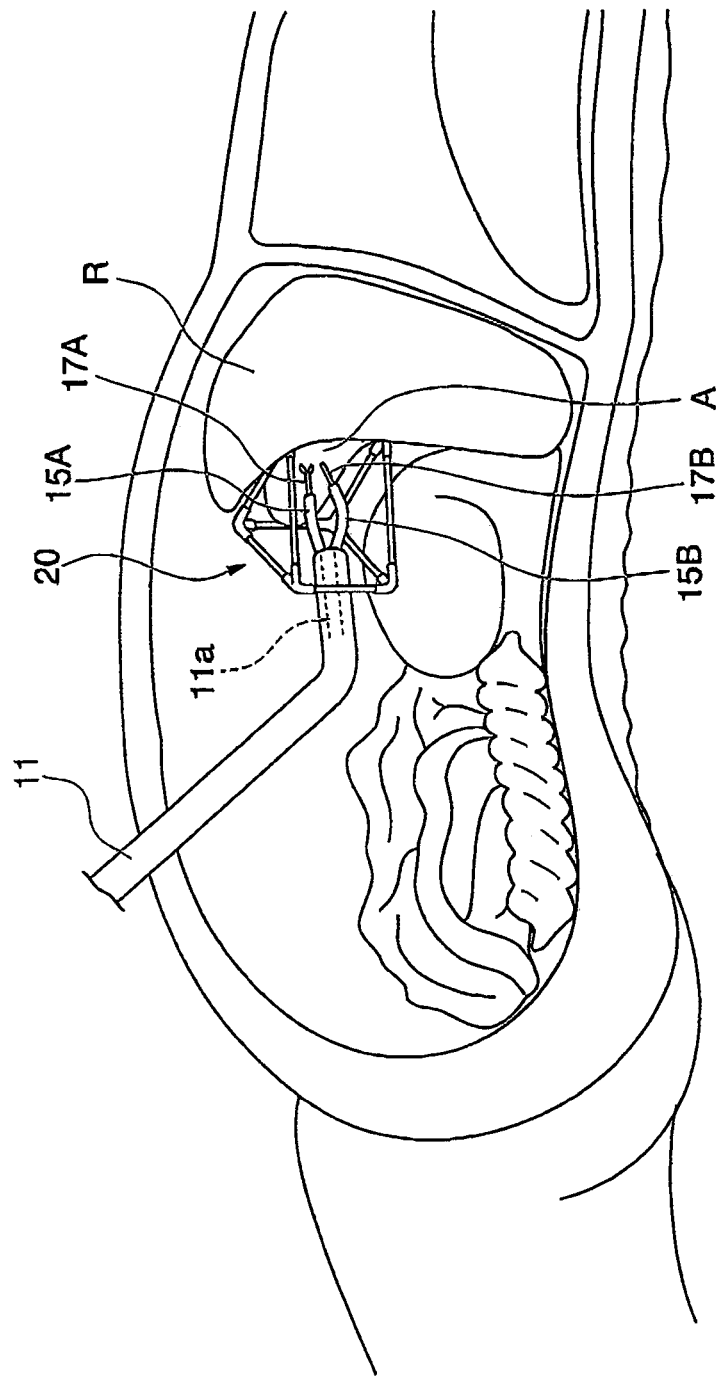
FIG. 2 is a partially sectional view showing an endoscopic surgical procedure using the surgical apparatus.

Next, as shown in FIG. 2, the enlarged spacial structure 20 is moved to a predetermined position in the abdominal cavity by using the treatment instruments 17A and 17B such as forceps or the like protruded from the distal end of the arms 15A and 15B. By the spacial structure 20 that is moved, the liver R is lifted and supported to be separated from the cholecyst A (step S4). Accordingly, the cholectst A is exposed inside of the abdominal cavity and a space that is necessary for the observation or the treatment is assured around the cholecyst A by the space of the spacial structure 20.

Then, the distal ends of an observation portion or the treatment instruments 17A and 17B located at the distal end of the insertion portion 11 are oriented to the cholecyst which is the pathological lesion by using the opening portion 24 of the spacial structure 20 (step S5).

Then, damaged condition of the cholecyst A is confirmed by the observation portion of the treatment endoscope 10 (step S6), an adequate treatment such as extraction or the like is operated in accordance with the damaged condition of the cholecyst A.

When the treatment to the cholecyst A is finished, the spacial structure 20 is recovered by using the channel 11a of the insertion portion 11. That is, a recovery instrument for the grasping forceps or the like is inserted into the channel 11 from the forceps plug 11b for example, the spacial structure 20 is locked by protruding a distal end of the recovery instrument from the distal end of the channel 11a. Then, the spacial structure 20 is retracted into the channel 11a by the recovery instrument. The spacial structure 20 shrinks while being folded by its own elasticity and is retracted into the channel 11a. Then, the spacial structure is retracted to the outside of the forceps plug 11b by passing through the channel 11.

Then, the treatment endoscope 1 is recovered with the treatment instruments 17A and 17B (step S8).

In accordance with the procedure, since the body tissues or the internal organs such as the liver R is supported by the spacial structure 20 enlarged in the body, it is possible to assure a space that is necessary for the observation or the treatment around the pathological lesion such as cholecyst A or the like located below the supported body tissues. By using the space, required treatments can be performed on the pathological lesion such as cholecyst A or the like.

Here, the spacial structure 20 can enlarge itself by its own elasticity without any operations from the outside of the body and support body tissues while maintaining the enlarged state. In this manner, since operations from the outside for enlarging the spacial structure 20 or maintaining the enlarged state are not necessary, it is possible to reduce the burden of operators, for example.

[Second Embodiment]

Figure 7:
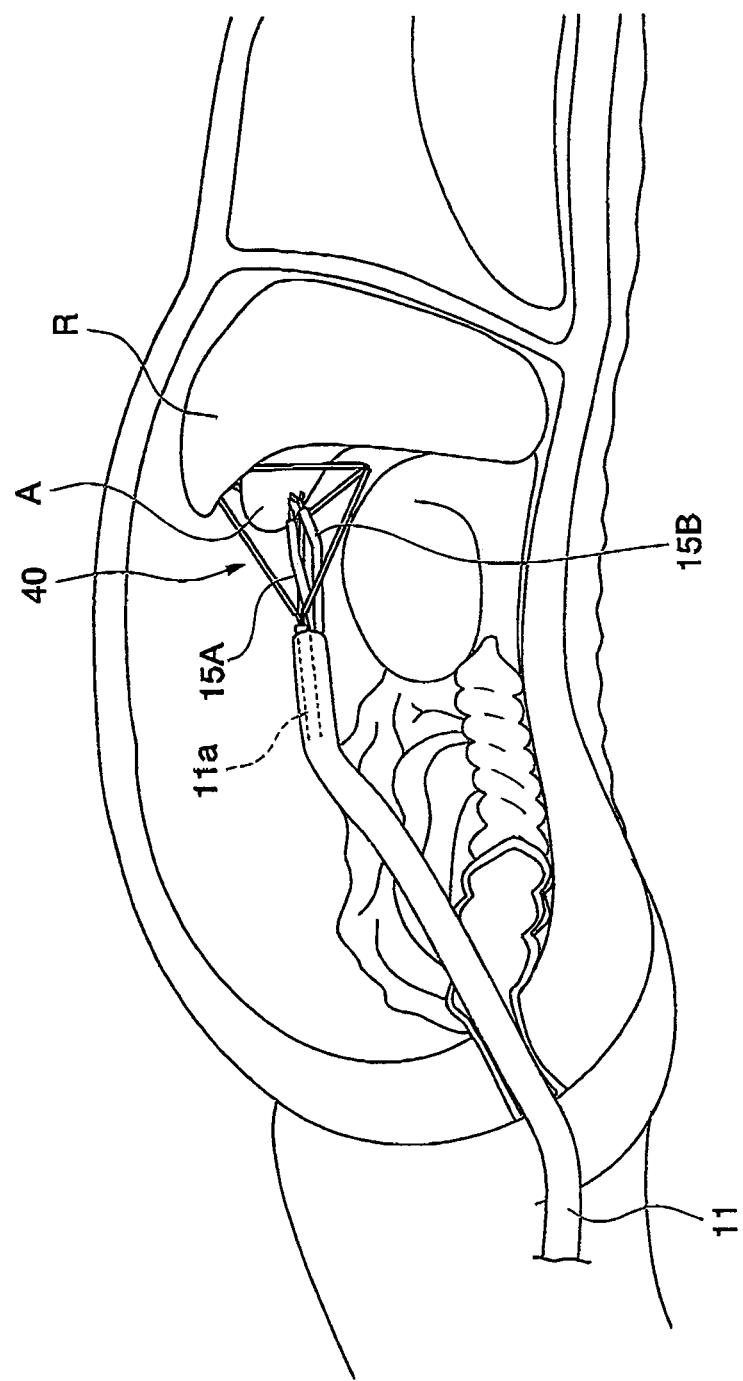
FIG. 7 is a partial sectional view showing an endoscopic surgical procedure using a surgical apparatus in accordance with a second embodiment.
Figure 8:
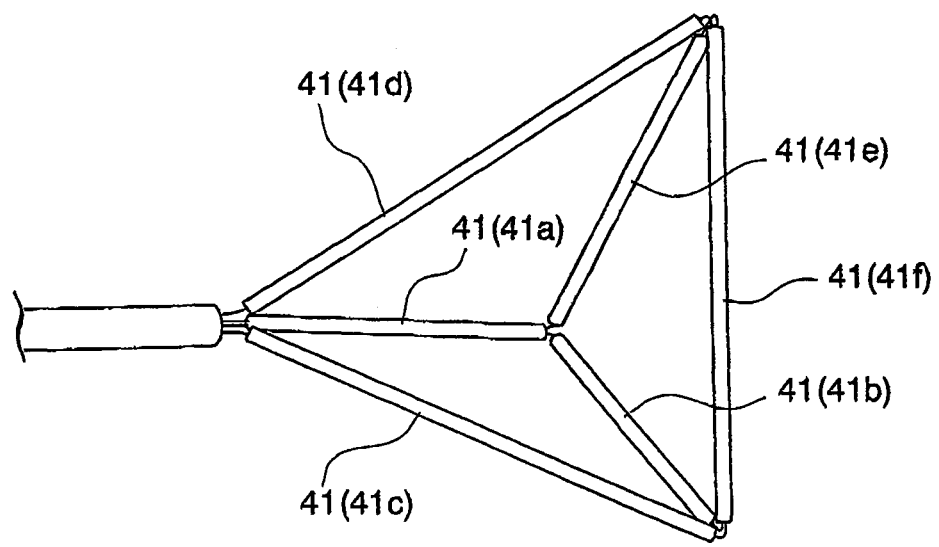
FIG. 8 is a perspective view showing a spacial structure used by the surgical apparatus in accordance with the second embodiment.

A second embodiment of the present invention shall be explained with reference to FIGS. 7 to 12. FIG. 7 is a partially cross sectional view showing an endoscopic surgical procedure using a surgical apparatus in accordance with a second embodiment of the present invention. Here, in the structural element of the second embodiment, the same reference numbers shall be given to identical portions and descriptions of overlapping portions with the first embodiment shall be omitted. This applies to a third embodiment and a fourth embodiment described later as well.

The second embodiment is different from the first embodiment in that a spacial structure using a different structure is used and the spacial structure is inserted into the abdominal cavity by penetrating a wall portion of the anus or the large intestine not using the umbilicus as the insertion portion of the treatment endoscope.

Figure 9:
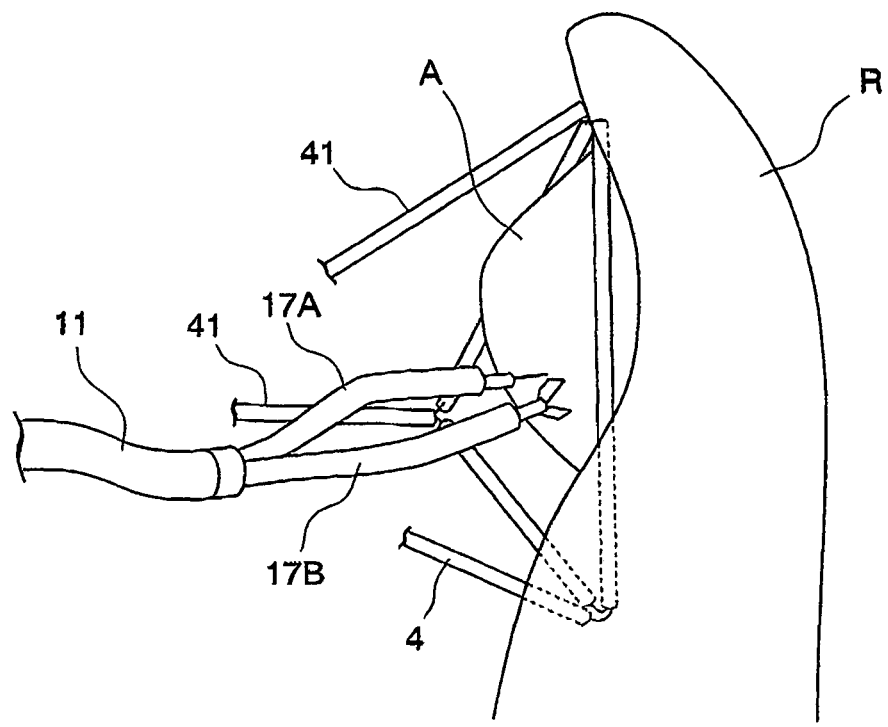
FIG. 9 is an enlarged perspective view showing the spacial structure in use which is used by the surgical apparatus in accordance with the second embodiment.
Figure 10:
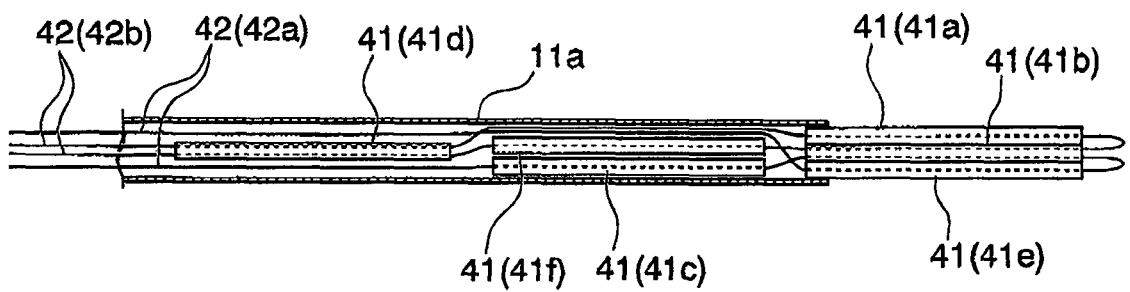
FIG. 10 is a cross sectional view showing the spacial structure used by the surgical apparatus in accordance with the second embodiment.

As shown in FIGS. 8 to 12, the spacial structure 40 of the embodiment, has a plurality of pipes 41 and wire 42 inserted through the pipes 41. Here, in the shown example, by connecting each of the pipes 41 via the wires 42, the spacial structure forms three-sided pyramids in the enlarged state. Also, the spacial structure 40 becomes substantially a line shape as shown in FIG. 10, when folded and shrunken.

Figure 12:
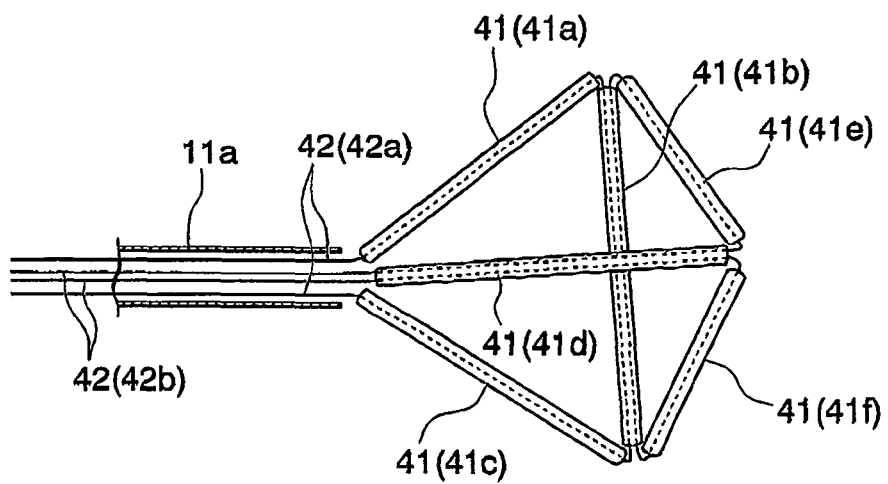
FIG. 12 is a view showing a procedure of enlarging the spacial structure used by the surgical apparatus in accordance with the second embodiment.

A relationship between the pipe 41 and the wire 42 shall be explained with reference to a usage state shown in FIG. 12 as an example. Two wires are used. The first wire 42a of the two wires is passed through the channel 11a of the insertion portion 11 of the treatment endoscope, inserted into a first pipe 41a, a second pipe 41b, and a third pipe 41c, and returned to the channel 11a again. Also, the other second wire 42b is passed through the channel 11a of the insertion portion 11 of the treatment endoscope, inserted into the fourth pipe 41d, a fifth pipe 41e, and the second pipe 41b, and also a sixth pipe 41f, and returned to the channel 11a. The pipe 41 is made of a hard material of relatively high rigidity such as stainless steel and rigid plastic for example. The wire 42 is made of a material with relatively high rigidity so that when pushed in the longitudinal direction, the suppress strength can be transmitted to the distal end thereof.

Next, a procedure for treating the cholecyst A which is the pathological lesion by using the above surgical apparatus shall be described. Here, explanations on identical processes explained in the first embodiment shall be omitted.

First, the distal end of the insertion portion 11 of the treatment endoscope 10 is inserted from a natural opening of the patient such as the anus to the large intestine, and is further inserted to the vicinity of the liver R in the abdominal cavity by penetrating the wall portion of the large intestine.

Next, the spacial structure 40 folded in advance is inserted from a forceps plug of the insertion portion 11, the spacial structure 40 is extruded from the distal end of the channel 11a by inserting and operating the distal ends of the wires 42a and 42b.

Figure 11:
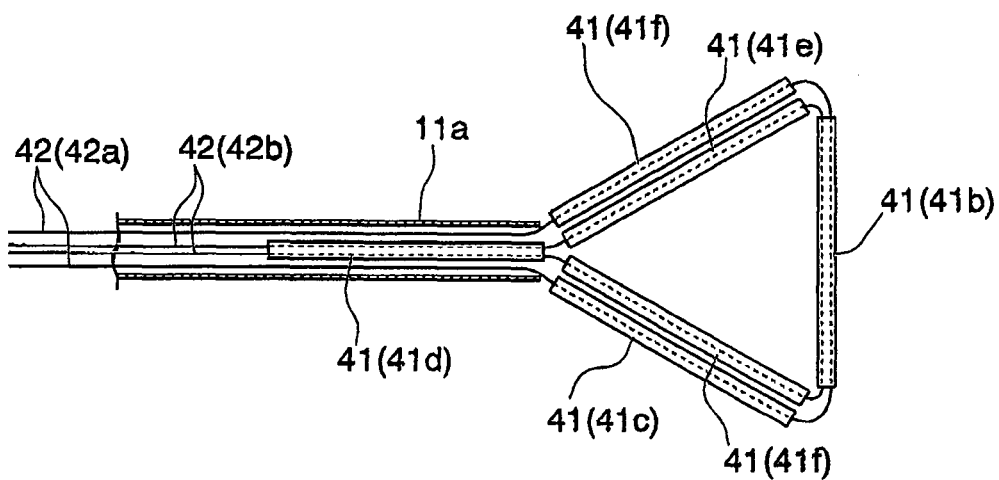
FIG. 11 is a view showing a procedure of enlarging the spacial structure used by the surgical apparatus in accordance with the second embodiment.

That is, by pushing the ends of the wires 42a and 42b forward respectively, first as shown in FIG. 10, the first pipe 41a, the fifth pipe 41e, and the second pipe 41b are extruded from the distal end of the channel 11a. Next, one side of the first wire 42a inserted through the first pipe 41a is no longer pushed, and the other side of the first wire 42a and both ends of the second wire 42b are pushed forward. Accordingly, as shown in FIG. 11, the third pipe 41c and the sixth pipe 41f are extruded from the distal end of the channel 11a. Next, both ends of the first wire 42a are no longer pushed, and both ends of the second wire 42b are pushed. Then, as shown in FIG. 12, the fourth pipe 41d is extruded from the distal end of the channel 11a. The three-sided pyramid is formed by these extruded six pipes 41. That is, it is possible to enlarge the spacial structure 40 in the abdominal cavity.

By moving the enlarged spacial structure 40 to the distal end of the treatment endoscope, the spacial structure 40 is moved to a predetermined position in the abdominal cavity. The liver R is supported by the spacial structure 40 so as to be apart from the cholecyst A. Accordingly, the cholecyst A is exposed in the abdominal cavity, and a space necessary for the observation or treatment is assured around the cholecyst A.

Then, as shown in FIGS. 7 and 9, distal ends of the observation portion and the treatment instruments 17A and 17B located at the distal end of the insertion portion 11 are oriented to the cholecyst A which is the pathological lesion by using the opening portion 44 of the spacial structure 40, confirms the damaged condition of the cholecyst A, and performs necessary treatments thereafter.

When the treatment to the cholecyst A is finished, the spacial structure 40 is recovered by using the channel 11a of the insertion portion 11. The recovering procedure of the spacial structure 40 is opposite to the enlarging procedure of the spacial structure 40.

That is, by extracting both ends of the second wire 42b to the proximal side, the fourth pipe 41d is stored in the channel 11a. Next, by extracting both ends of the second wire 42b and one side of the first wire 42a (a side the third pipe 41c is inserted) in the proximal side, the fourth pipe 42d is extracted to the further proximal side of the channel 11a, and the third pipe 41c and the sixth pipe 41f are stored in the channel 11a. Furthermore, by further extracting both ends of the first wire 42a and the second wire 42b respectively to the proximal side, it is possible to store the first pipe 41a, the second pipe 41b, and the fifth pipe 41e in the channel 11a.

Next, the treatment endoscope 1 is recovered with the spacial structure 40 and the treatment instruments 17A and 17B stored in the channel 11a.

Here, in the above described embodiment, the spacial structure 40 composed of pipe and wire is directly inserted into the channel 11a of the insertion portion 11. However, the embodiment is not limited to this but the spacial structure 40 may be first stored in the sheath, and the then spacial structure may be inserted into the channel with the sheath.

[Third Embodiment]

Figure 13:
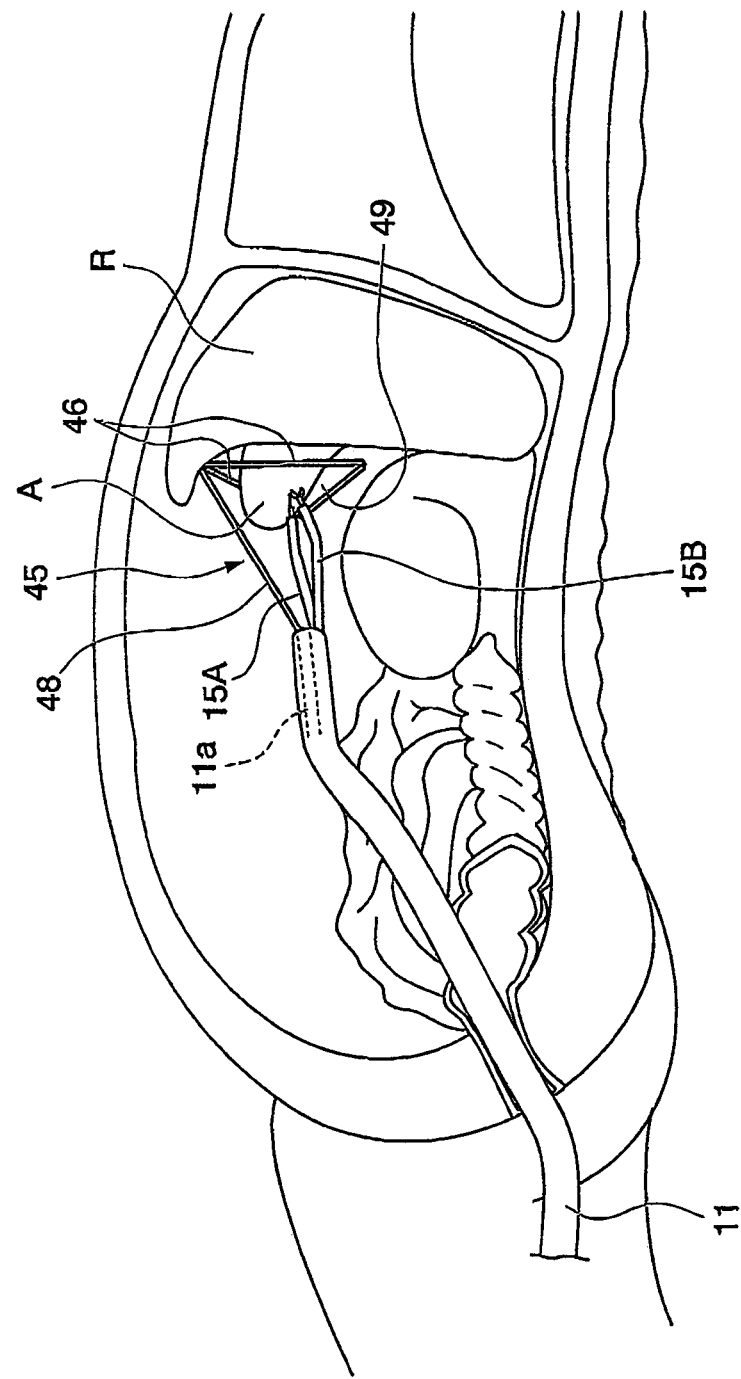
FIG. 13 is a partial sectional view showing endoscopic surgical procedure using a surgical apparatus in accordance with a third embodiment.

A third embodiment of the present invention shall be explained with reference to FIGS. 13 to 15. FIG. 13 is a partially cross sectional view showing an endoscopic surgical procedure using a surgical apparatus in accordance with a third embodiment of the present invention.

The third embodiment is different from the second embodiment in that a spacial structure 45 using a different structure is used.

Figure 14:
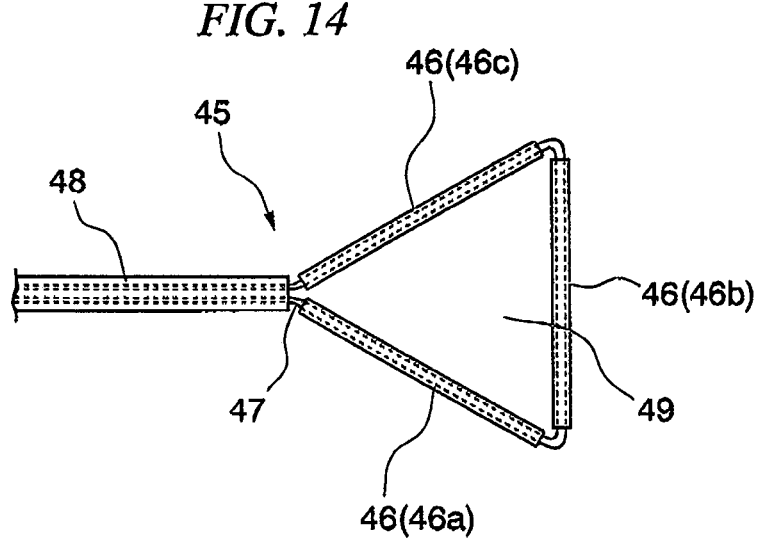
FIG. 14 is a perspective view showing a spacial structure used by the surgical apparatus in accordance with the third embodiment.

As shown in FIGS. 13 and 14, a spacial structure 45 of the present embodiment has a plurality of pipes 46, a wire 47 inserted through the pipes 46, and a sheath 48 capable of storing the wire and the pipe. In a shown example, in the enlarged usage state, the spacial structure 40 forms a triangle with pipes by connecting three pipes 46 through one wire 47. Also, the spacial structure 45 becomes substantially a line shape as shown in FIG. 15, when folded and shrunken.

A relationship between the pipe 46 and the wire 47 shall be explained with reference to a usage state in FIG. 13. One side of the wire 47 protrudes from the distal end of the sheath 48, inserted into a first pipe 46a, a second pipe 46b, and a third pipe 41c, and is returned to the sheath 48 again. Both ends of the wire 47 protrude outward from a proximal end of the sheath 48, therefore, it is possible to push and extract only the wire 47. The sheath 48 is inserted into the channel 11a of the insertion portion 11 of the treatment endoscope. The pipe 46 is made of a hard material of relatively high rigidity such as stainless steel and rigid plastic for example. The wire 47 is made of a material with relatively high rigidity so that when pushed in the longitudinal direction, the force can be transmitted to the distal end thereof.

Figure 15:
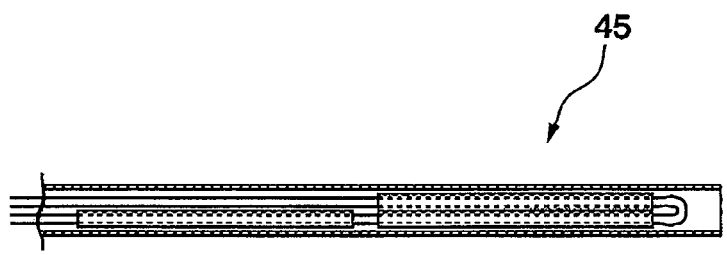
FIG. 15 is a cross sectional view showing the spacial structure in a stored state which is used by the surgical apparatus in accordance with the third embodiment.

In accordance with the surgical apparatus of the third embodiment, the spacial structure 45, folded in advance as shown in FIG. 15, is extruded from the distal end of the channel 11a of the insertion portion 11.

That is, the distal end of the sheath 48 is disposed in substantially the same position as the distal end of the insertion portion 11 of the treatment endoscope, with this state, a middle portion of the wire 47 is pushed forward. Then, as shown in FIG. 14, the first pipe 46a, the second pipe 46b, and the third pipe 46c are extruded from the distal end of the sheath 48, and those pipes form a triangle. Next, after abutting the position of the second pipe 46b to an adequate position of the body tissue, the distal end portion of the sheath 48 is extruded from the distal end of the channel 11a. Then, as shown in FIG. 13, the plane of the triangle is substantially along the axis of the sheath 48 and is bent away from the axis of the sheath 48 at an apex of the triangle being pushed. Therefore, it is possible to lift and support the liver R so as to be separated from the cholecyst by the spacial structure 45 in which the pipes form a triangle in a bent state. Accordingly, the cholecyst is exposed inside of the abdominal cavity, and a space necessary for the observation or the treatment is assured around the cholecyst.

Next, distal ends of the observation portion and the treatment instrument located at the distal end of the insertion portion 11 are oriented to the cholecyst which is the pathological lesion by using the opening portion 49 of the spacial structure 45, confirms the damaged condition of the cholecyst, and performs necessary treatments thereafter.

When the treatment to the cholecyst is finished, the spacial structure 45 is recovered by using the channel 11a of the insertion portion 11. The recovering procedure of the spacial structure 45 is opposite to the enlarging procedure of the spacial structure 45.

That is, by retracting the sheath 48 to the proximal side, the sheath 48 is stored in the channel 11a. Next, by retracting both ends of the wire 47 to the proximal side, the first pipe 46a, the second pipe 46b, and the third pipe 46c are respectively stored in the sheath 48, and then the sheath 48 is stored in the channel 11a.

[Fourth Embodiment]

Figure 16:
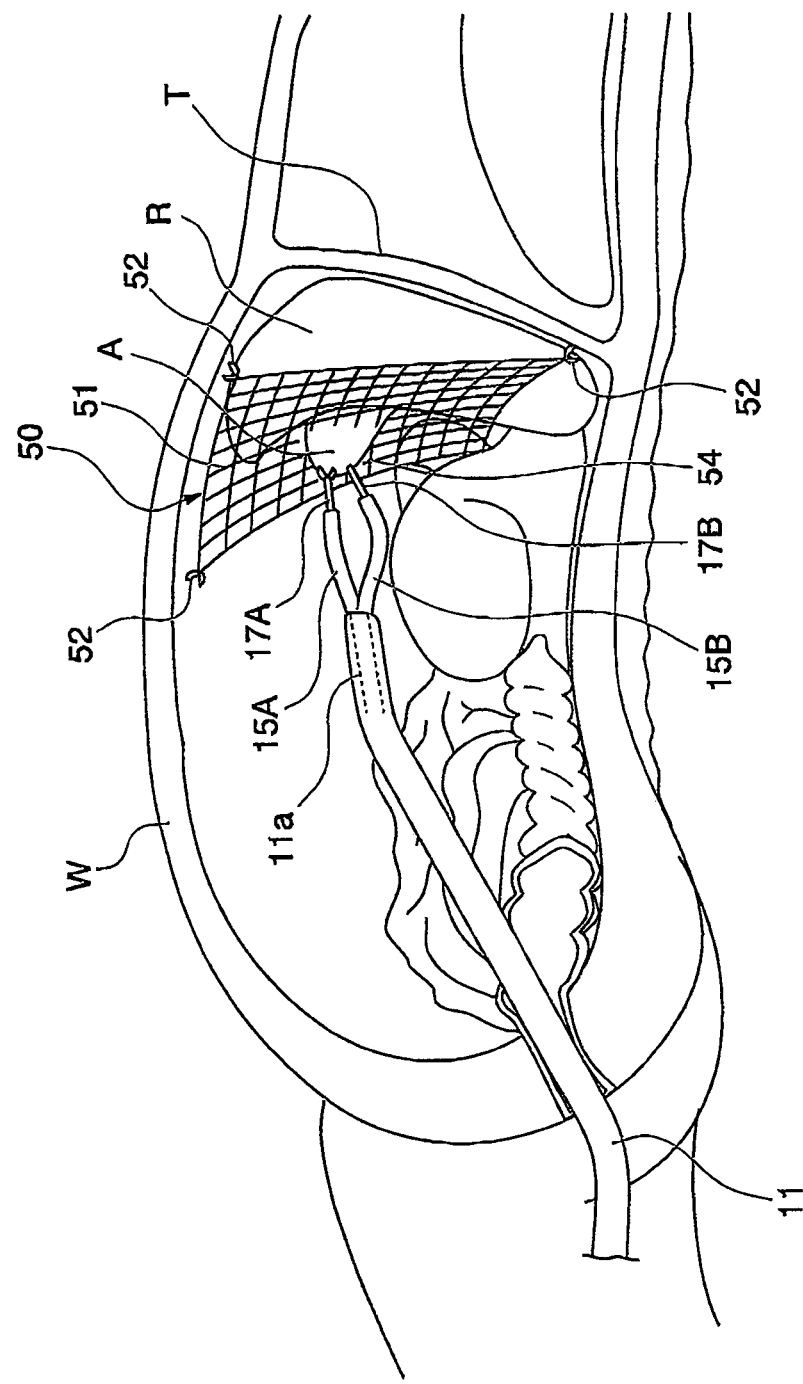
FIG. 16 is a partial sectional view showing endoscopic surgical procedure using a surgical apparatus in accordance with a fourth embodiment.

A fourth embodiment of the present invention shall be explained with reference to FIGS. 16 to 17. FIG. 16 is a partially cross sectional view showing an endoscopic surgical procedure using a surgical apparatus in accordance with a fourth embodiment of the present invention.

The fourth embodiment is different from the first embodiment in that a spacial structure 50 using a different structure is used, and the spacial structure is inserted into the abdominal cavity by penetrating a wall portion of the anus or the large intestine not using the umbilicus as the insertion portion of the treatment endoscope.

As shown in FIG. 16, the spacial structure 50 of the embodiment, has a mesh member 51, a fixture 52 for fixing the mesh member 51 in an enlarged state to the tissues inside of the body cavity.

The mesh member 51 is made of silicon system materials, for example, which are flexible and harmless to the human body. As the mesh member, in the figure, a quadrangular grid is used for a basic shape, but it is not limited to this. The basic shape may be a triangle or hexagon.

The fixture 52 is attached to a predetermined position of the mesh member 51 in advance. A member used for a clip, which is able to grasp a portion of a biological tissue by a biasing force of a spring or the like, is used for the fixture 52 for example. The fixture 52 may be a wedge shape which is attached to a predetermined position of the mesh member 51 in advance, and be inserted and fixed to a biological tissue.

Next, a surgical procedure for treating the cholecyst A which is a pathological lesion by using the surgical apparatus of the above structure shall be explained. Explanations on the identical process to the process of the first embodiment shall be omitted.

First, the distal end of the insertion portion 11 of the treatment endoscope 10 is inserted from a natural opening of the patient such as the anus to the large intestine, and is further inserted to the vicinity of the liver R in the abdominal cavity by penetrating the wall portion of the large intestine.

Next, the spacial structure 50 folded in advance is inserted from a forceps plug of the insertion portion 11, and the pushing instrument such as the wire is inserted, and the spacial structure 50 is sent into the abdominal cavity by pushing the spacial structure 50 through the channel 11a. The spacial structure 50 extruded into the abdominal cavity from the channel 11a is slightly enlarged by its own elasticity.

Next, by using the treatment instruments 17A and 17B protruding from the distal end of the insertion portion 11 of the treatment endoscope 1, the plurality of fixtures 52 is fixed to the biological tissues such as the abdominal wall W or the diaphragm T, and the spacial structure is set to the enlarged state. By the mesh member 51 of the enlarged spacial structure 50, the biological tissue, which is not the treatment target such as the liver R, is directly supported. Here, as the method of supporting the biological tissue or the internal organs, which is not the treatment target such as the liver or the like, using a grasping member such as the clip attached to the mesh member 51 is also available other than directly supporting the biological tissue or the internal organs, which is not the treatment target such as the liver or the like, by the mesh member 51.

As described above, in the case of directly supporting the biological tissue or the internal organs, which is not the treatment target such as the liver or the like, by the mesh member 51, as shown in FIG. 16, a portion of the mesh member 51 is dissected by a treatment instrument for dissection. Accordingly, it is possible to expose the cholecyst A, which is the treatment target, closer to the treatment endoscope than the mesh member. Also, it is possible to assure a space necessary for the observation or the treatment around the cholecyst A by the space inside of the spacial structure 50.

Then, the distal ends of the observation portion and the treatment instruments 17A and 17B located at the distal end of the insertion portion 11 are oriented to the cholecyst A, which is the pathological lesion, by using an opening portion 54 of the spacial structure 50, confirms the damaged condition of the cholecyst A, and performs necessary treatments thereafter.

When the treatment to the cholecyst A is finished, the spacial structure 50 is recovered by using the channel 11a of the insertion portion 11.

That is, a recovery instrument for the grasping forceps, for example, is inserted into the channel 11a from the forceps plug 11b, the distal end of the recovery instrument is locked to the spacial structure 50, and the spacial structure 50 is retracted into the channel 11a.

Then, the treatment instrument 1 is recovered with the spacial structure and the treatment instruments 17A and 17B stored in the channel.

In accordance with the procedure, since the body tissue is supported by the spacial structure 50 enlarged in the body, it is possible to assure a space that is necessary for the observation or the treatment around the pathological lesion such as the cholecyst A or the like located below the supported body tissues. By using the space, required treatments can be operated to the pathological lesion such as cholecyst A or the like.

Since the spacial structure 50 is composed mainly of the mesh member 51 which is freely deformable, it is possible to support in arbitral shape the internal organs or the like, which are not the treatment target, it is easier to assure the space for the treatment as a result.

Also, since it is possible to support a plurality of biological tissues at once, it is possible to assure a large space for the treatment around the biological tissue which is the treatment target; additionally it is possible to operate procedures in a plurality of locations.

Furthermore, the spacial structure 50 is configured mainly by the mesh member 51 which is the mesh member flexible in itself, it is possible to dispose the spacial structure 50 in an arbitrary location in the body cavity. Also, since the size of the spacial structure 50 is large, it is advantageous in that it is easy to confirm that the spacial structure 50 is left behind in the body or not.

Figure 17:
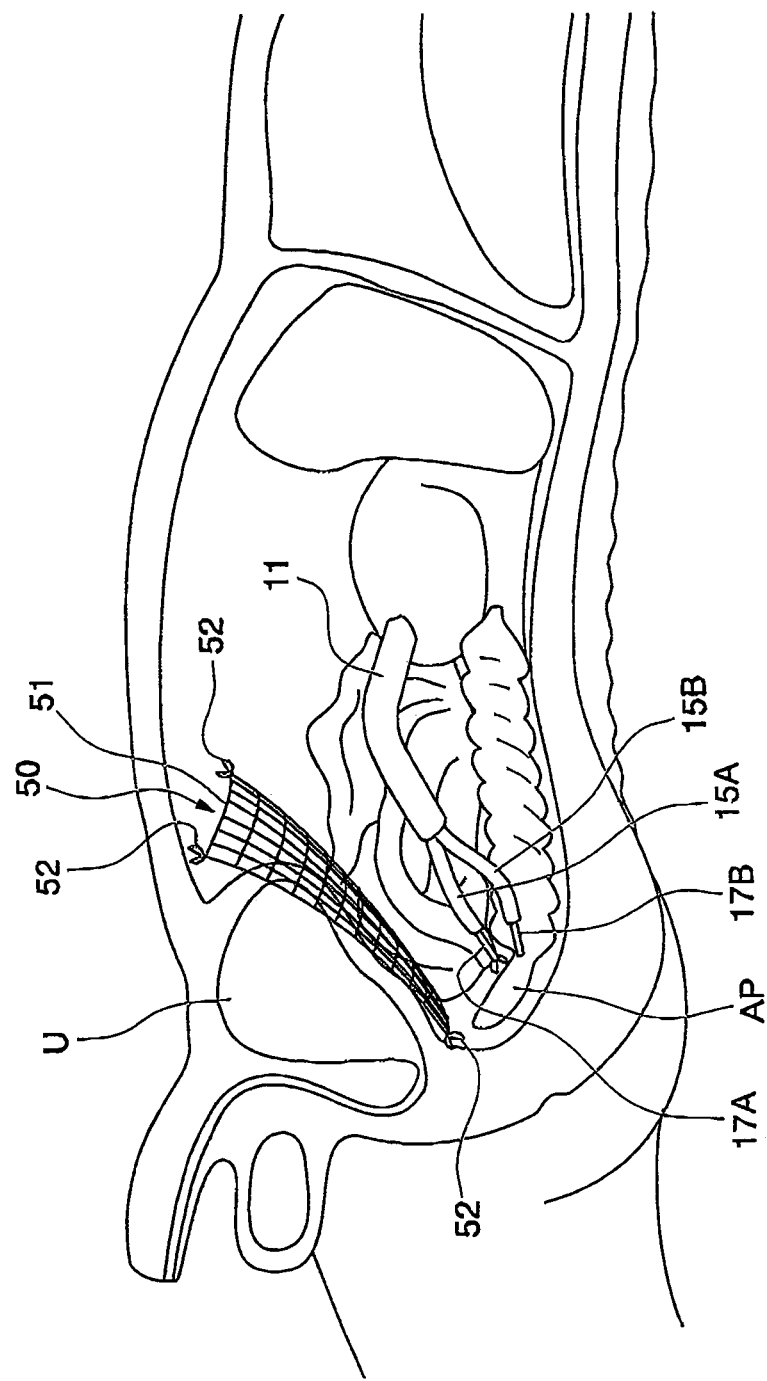
FIG. 17 is a partial sectional view showing another example of the endoscopic surgical procedure using the surgical apparatus in accordance with the fourth embodiment.

FIG. 17 shows an alternative example of the fourth embodiment.

In this example, by the spacial structure 50 composed of the mesh member 51 and the fixture 52, the bladder U is supported and the appendico AP located below the bladder U is treated. The insertion portion 11 of the treatment endoscope 1 is inserted into the body cavity from the mouth, for example, passes the esophagus and stomach, penetrates the stomach wall and reaches the inside of the abdominal cavity. Since the spacial structure 50 is made mainly of mesh member and is flexible, it is possible to introduce the spacial structure into the body cavity passing through the natural orifices, for example, by mouth, where only a relatively small curvature radius is available.

As described above, preferred embodiments of the present invention are described. However, the present invention shall not be limited to the embodiments. Various changes, such as adding, omitting, or alternating the structural elements are possible, provided they do not depart from the scope of the present invention.

For example, in the present embodiment, the spacial structure is inserted into the body cavity via the channel 11a of the insertion portion 11 of the treatment endoscope, it is not limited to this. For example, a special instrument made of a pipe member for inserting the spacial structure into the body cavity is prepared, and the spacial structure may be introduced into the body cavity by using the special instrument.

In FIGS. 1 and 2, examples in the case of using the grasping forceps and the dissection knife are shown, but the embodiment is not limited to those. Other treatment instruments such as a rotating grip, a high-frequency snare, a balloon, or the like may be used in accordance with treatment relative to the pathological lesion.

Also, in the above embodiments, the treatment endoscope 1, in which two treatment instruments can be introduced into the insertion portion 11, is used, but it is not limited to this. A treatment endoscope, in which only one treatment instrument can be introduced, may be used, or the endoscope may only have an observation function, and the treatment instrument may be introduced into the body cavity by using another pipe line.

The above embodiments are described by treating the cholecyst A or the appendico AP for example, but it is not limited to this. The present invention can also be applied to cases in which the treatment is operated by using the spacial structure in the digestive canal.

Also, the spacial structure may support the tissue inside of the body cavity, which is not the treatment target, by introducing air therein.

What is claimed is:

1. A surgical apparatus comprising:
a spatial structure deformable to be shrunken or enlarged, in which it is possible to support tissues inside of a body cavity and to be placed in a body, when it is disposed in the body cavity in the enlarged state, wherein
the spatial structure is arranged in a channel of an insertion portion which is capable of being inserted into the body cavity in the shrunken state;
the spatial structure comprises a first plurality of tubular members and a second plurality of tubular members, with the tubular members being movable along a longitudinal axis of the channel, and a wire which is inserted into at least several of the plurality of tubular members, are capable of moving with respect to the plurality of tubular members and extended so as to freely advance or retract from a distal end portion to a proximal end portion of the channel;
when the spatial structure is shrunken, the plurality of tubular members are stored in the channel along the longitudinal axis thereof; and
when the wire is projected from the distal end of the insertion portion and the spatial structure is enlarged at a position projected from the distal end of the insertion portion, the spatial structure includes a space that is defined by the first plurality of tubular members and the second plurality of tubular members,
the first plurality of tubular members protrude from an opening of the distal end of the insertion portion, angled with respect to the longitudinal axis of the channel, and
the second plurality of tubular members are connected with distal ends of the first plurality of tubular members via the wire and the second tubular members form a triangle that defines an opening which faces the opening of the distal end of the insertion portion.

2. The surgical apparatus in accordance with claim 1, wherein at least a part of the spatial structure is provided with a flat portion which is able to abut the tissues inside of the body cavity.

3. The surgical apparatus in accordance with claim 1, wherein the plurality of tubular members are made of hard material.

4. The endoscope surgical procedure in accordance with claim 1, wherein
- the spatial structure defines a three-sided pyramid using three first tubular members and three second tubular members for each side of the three sided pyramid,
- the space is formed inside the three-sided pyramid,
- the triangle is configured by the three second tubular members, and
- the three first tubular members are arranged toward each corner of the triangle from the distal end of the insertion portion so as to support the opening defined by the triangle.

* * * * *